United States Patent
Cittadino

(10) Patent No.: US 7,648,127 B2
(45) Date of Patent: Jan. 19, 2010

(54) AIR FRESHENER DEVICE AND METHODS FOR CONTROLLING AN AMOUNT OF EVAPORATED SCENTED MATERIAL EMITTED FROM THE AIR FRESHENER DEVICE

(75) Inventor: Antonio M. Cittadino, Appleton, WI (US)

(73) Assignee: Georgia-Pacific Consumer Products LP, Atlanta, GA (US)

( * ) Notice: Subject to any disclaimer, the term of this patent is extended or adjusted under 35 U.S.C. 154(b) by 82 days.

(21) Appl. No.: 12/016,693

(22) Filed: Jan. 18, 2008

(65) Prior Publication Data

US 2009/0184432 A1 Jul. 23, 2009

(51) Int. Cl.
*B01F 3/04* (2006.01)

(52) U.S. Cl. .................. 261/26; 222/187; 261/104; 261/DIG. 88

(58) Field of Classification Search .............. 261/24, 261/26, 30, 104, 107, DIG. 17, DIG. 65, 261/DIG. 88, DIG. 89; 96/222; 222/187; 422/5, 28, 122–124

See application file for complete search history.

(56) References Cited

U.S. PATENT DOCUMENTS

| | | | | |
|---|---|---|---|---|
| 4,166,087 A | * | 8/1979 | Cline et al. | 261/96 |
| 5,029,729 A | * | 7/1991 | Madsen et al. | 222/1 |
| 5,038,972 A | | 8/1991 | Muderlak et al. | |
| 5,078,046 A | * | 1/1992 | Mascolo et al. | 454/157 |
| 5,078,971 A | * | 1/1992 | Matuda et al. | 422/121 |
| 5,126,078 A | * | 6/1992 | Steiner et al. | 261/26 |
| 5,223,182 A | * | 6/1993 | Steiner et al. | 261/26 |
| 5,324,490 A | * | 6/1994 | Van Vlahakis et al. | 422/305 |
| 5,342,584 A | | 8/1994 | Fritz et al. | |
| RE34,847 E | | 2/1995 | Muderlak et al. | |
| 5,498,397 A | * | 3/1996 | Horng | 422/124 |
| 5,759,451 A | * | 6/1998 | Tomasiak et al. | 261/23.1 |
| 5,799,826 A | * | 9/1998 | Brown et al. | 222/4 |
| 5,823,390 A | | 10/1998 | Muderlak et al. | |
| 5,908,140 A | | 6/1999 | Muderlak et al. | |
| 5,994,808 A | | 11/1999 | Gross et al. | |
| 6,394,310 B1 | | 5/2002 | Muderlak et al. | |
| 6,443,434 B1 | | 9/2002 | Prather | |
| 6,581,915 B2 | * | 6/2003 | Bartsch et al. | 261/26 |
| 6,592,104 B2 | | 7/2003 | Cox | |
| 6,637,729 B2 | * | 10/2003 | Gordon | 261/26 |
| 6,769,580 B2 | | 8/2004 | Muderlak et al. | |
| 6,913,733 B2 | | 7/2005 | Hardy et al. | |
| 7,223,166 B1 | | 5/2007 | Wiseman, Sr. et al. | |
| 2005/0191217 A1 | | 9/2005 | Selander | |
| 2005/0191269 A1 | | 9/2005 | Glassco | |
| 2005/0275118 A1 | * | 12/2005 | Chen | 261/30 |
| 2007/0036673 A1 | | 2/2007 | Selander | |

* cited by examiner

*Primary Examiner*—Richard L Chiesa
(74) *Attorney, Agent, or Firm*—Joel T. Charlton

(57) ABSTRACT

A method for controlling an amount of evaporated scented material emitted from an air freshener device include generating a first control signal to induce the motor to rotate fan blades at a first rotational speed during a first time interval which urges air flow toward the aperture of the container to induce evaporation of the scented material in the container. The method further includes generating additional control signals to induce the motor to increase a rotational speed of the fan blades during a second time interval to increase air flow toward the aperture of the container, the second time interval being after the first time interval, such that first and second mass rates of evaporated scented material from the container during the first and second time intervals, respectively, are maintained within a predetermined mass rate range.

14 Claims, 9 Drawing Sheets

AIR FRESHENER DEVICE AND METHODS FOR CONTROLLING AN AMOUNT OF EVAPORATED SCENTED MATERIAL EMITTED FROM THE AIR FRESHENER DEVICE

BACKGROUND OF THE INVENTION

Air fresheners have been utilized to dispense scented material. A problem, however, with the air fresheners is that an amount of dispensed scented material decreases dramatically over an operational life of the air fresheners.

Accordingly, the inventors herein have recognized a need for an improved air freshener device which reduces and/or eliminates the above-identified deficiency.

BRIEF DESCRIPTION OF THE INVENTION

A method for controlling an amount of evaporated scented material emitted from an air freshener device in accordance with an exemplary embodiment is provided. The air freshener device has a container, a motor, and fan blades coupled to the motor. The container has an aperture and holding a scented material therein. The method includes generating a first control signal to induce the motor to rotate the fan blades at a first rotational speed during a first time interval which urges air flow toward the aperture of the container to induce evaporation of the scented material in the container. The method further includes generating additional control signals to induce the motor to increase a rotational speed of the fan blades during a second time interval to increase air flow toward the aperture of the container, the second time interval being after the first time interval, such that first and second mass rates of evaporated scented material from the container during the first and second time intervals, respectively, are maintained within a predetermined mass rate range.

An air freshener device in accordance with another exemplary embodiment is provided. The air freshener device includes a container holding scented material therein. The container has an aperture. The air freshener device further includes a motor coupled to fan blades. The motor is configured to rotate the fan blades. The air freshener device further includes a controller operably coupled to the motor. The controller is configured to generate a first control signal to induce the motor to rotate the fan blades at a first rotational speed during a first time interval which urges air flow toward the aperture of the container to induce evaporation of the scented material in the container. The controller is further configured to generate additional control signals to induce the motor to increase a rotational speed of the fan blades during a second time interval to increase air flow toward the aperture of the container, the second time interval being after the first time interval, such that first and second mass rates of evaporated scented material from the container during the first and second time intervals, respectively, are maintained within a predetermined mass rate range.

A method for controlling an amount of evaporated scented material emitted from an air freshener device in accordance with another exemplary embodiment is provided. The air freshener device has a container, a motor, and fan blades coupled to the motor. The container has an aperture and holding a scented material therein. The method includes generating a first set of control signals to induce the motor to rotate the fan blades for a first percentage of time during a first time interval which urges air flow toward the aperture of the container to induce evaporation of the scented material in the container. The method further includes generating a second set of control signals to induce the motor to rotate the fan blades for a second percentage of time during a second time interval which urges air flow toward the aperture of the container to induce evaporation of the scented material in the container, the second time interval being after the first time interval, the second percentage of time being greater than the first percentage of time, such that first and second mass rates of evaporated scented material from the container during the first and second time intervals, respectively, are maintained within a predetermined mass rate range.

An air freshener device in accordance with another exemplary embodiment is provided. The air freshener device includes a container holding scented material therein. The container has an aperture. The air freshener device includes a motor coupled to fan blades. The motor is configured to rotate the fan blades. The air freshener device further includes a controller operably coupled to the motor. The controller is configured to generate a first set of control signals to induce the motor to rotate the fan blades for a first percentage of time during a first time interval which urges air flow toward the aperture of the container to induce evaporation of the scented material in the container. The controller is further configured to generate a second set of control signals to induce the motor to rotate the fan blades for a second percentage of time during a second time interval which urges air flow toward the aperture of the container to induce evaporation of the scented material in the container, the second time interval being after the first time interval, the second percentage of time being greater than the first percentage of time, such that, the first and second mass rates of evaporated scented material from the container during the first and second time intervals, respectively, are maintained within a predetermined mass rate range.

DETAILED DESCRIPTION OF THE INVENTION

Figure 1:
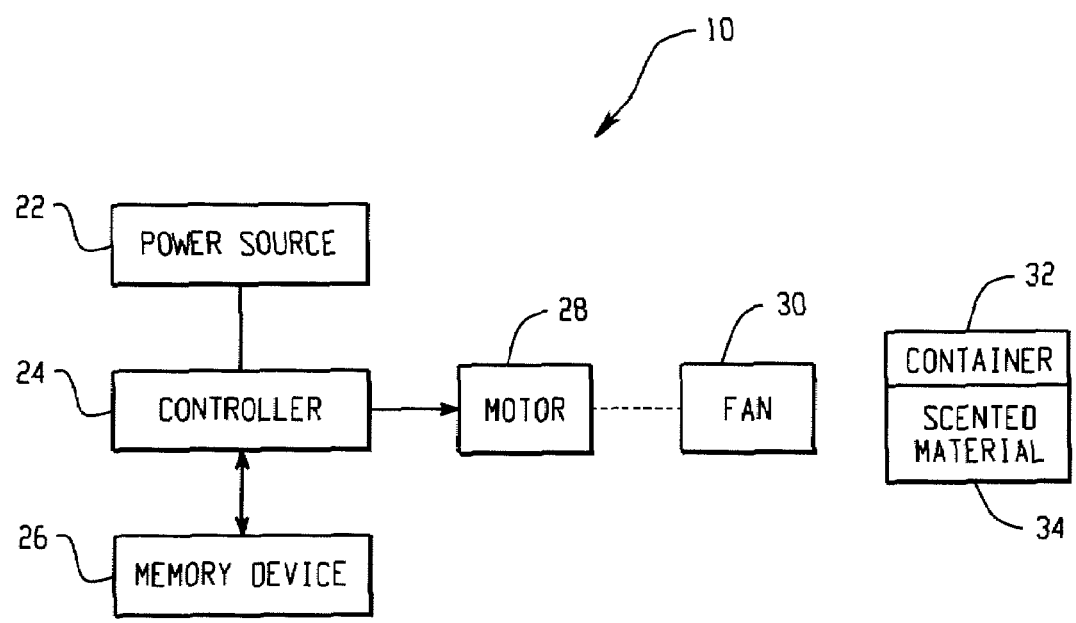
FIG. 1 is a schematic of an air freshener device in accordance with an exemplary embodiment.

Referring to FIG. 1, an air freshener device 10 for emitting evaporated scented material 34 is illustrated. The air freshener device 10 includes a housing 20 (FIG. 2), a power source 22, a controller 24, a memory device 26, a motor 28, a fan 30, and a container 32 holding scented material 34 therein.

Referring to FIGS. 1-4, the housing 20 is provided to hold the controller 24, the memory device 26, the motor 28, the fan 30, and the container 32 therein. The housing 20 includes a back plate 50 and a cover 52. The back plate 50 is configured to be mounted to a wall. The back plate 50 is further configured to hold the motor 28, the fan 30, and the container 32 thereon. When the power source 22 comprises batteries 60, 62, the back plate 50 is further configured to hold the batteries 60, 62 thereon. The cover 52 is rotatably coupled to the back plate 50. The cover 52 and the back plate 50 define an interior region for receiving the remaining components of the air freshener device 10 therein. Further, the cover 52 and the back plate 50 define gaps 54, 55, 56 for allowing evaporated scented material 34 to exit the housing 20. In one exemplary embodiment, the back plate 50 and the cover 52 are constructed from plastic.

The power source 22 provides an operational voltage to the controller 24. In one exemplary embodiment, the power source 22 comprises batteries 60, 62 which are electrically coupled in series to the controller 24 and provide an operational voltage to the controller 24. In another exemplary embodiment, the power source 22 comprises an electrical wall cube (not shown) and provides an operational voltage to the controller 24.

The controller 24 is provided to control operation of the motor 28. In particular, the controller 24 is configured to generate control signals for controlling operation of the motor 28, utilizing software algorithms stored in the memory device 26, which will be explained in greater detail below.

The motor 28 is provided to rotate fan blades 68, 70 in the fan 30 in response to control signals from the controller 24. The motor 28 includes a rotor 64 which is operably coupled to the fan blades 68, 70. In one exemplary embodiment, the motor 28 comprises a DC electric motor. However, in alternative embodiments, the motor 28 can comprise other types of electrical motors known to those skilled in the art.

The fan 30 is provided to urge air flow toward aperture 80 of the container 32 to evaporate scented material 34 held within the container 32. The fan 30 includes a cover portion 66 and fan blades 68, 70 disposed within the cover portion 66. The fan blades 68, 70 are operably coupled to the rotor 64 of the motor 28 and urge air flow toward the aperture 80 when the rotor 64 rotates the fan blades 68, 70.

The container 32 is provided to hold the scented material 34 therein. The container 32 has aperture 80 extending therethrough. The scented material 34 comprises a least one of a scented gel, a scented liquid, a scented solid material, and a scented semi-solid material. During operation, when air flow is directed toward the aperture 80, a portion of the scented material 34 within the container 32 evaporates and exits the gaps 54, 55, and 56 of the housing 20.

Before providing a detailed explanation of a first method for controlling amount of evaporated scented material 34 emitted from the air freshener device 10, a brief overview of the methodology will be explained. The inventor herein has recognized that by increasing a rotational speed of the fan 30 in the air freshener device 10 over an operational life of the air freshener device 10, a mass rate of evaporated scented material 34 from the air freshener device 10 can be maintained within a predetermined or desired mass rate range. In other words, the inventor herein has recognized that by increasing a rotational speed of the fan 30 over the operational life of the air freshener device 10, the scent load or detectable scent emitted from the air freshener device 10 can be maintained within a desired scent load range. In one exemplary embodiment, the rotational speed of the fan 30 is non-linearly increased over the operation life of the air freshener device 10.

Figure 5:
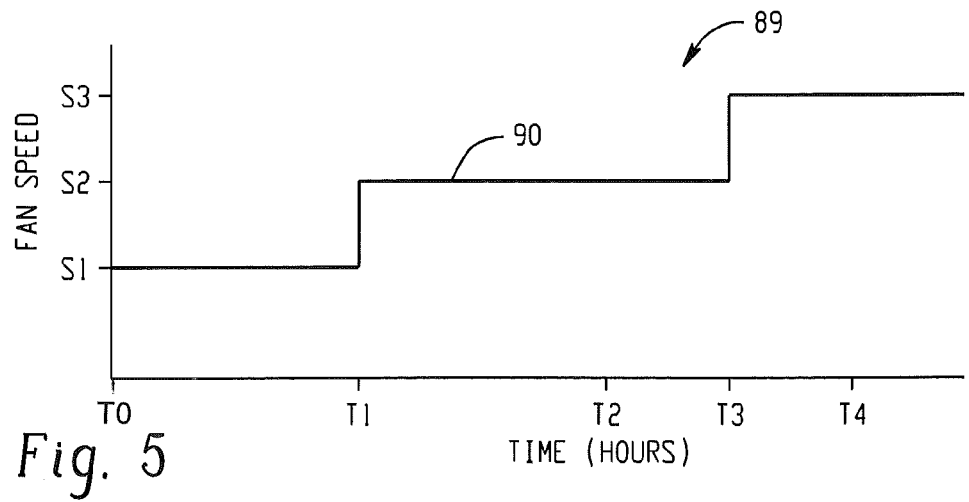
FIG. 5 is a graph having a curve illustrating exemplary fan speeds over time associated with the air freshener device of FIG. 1.
Figure 6:
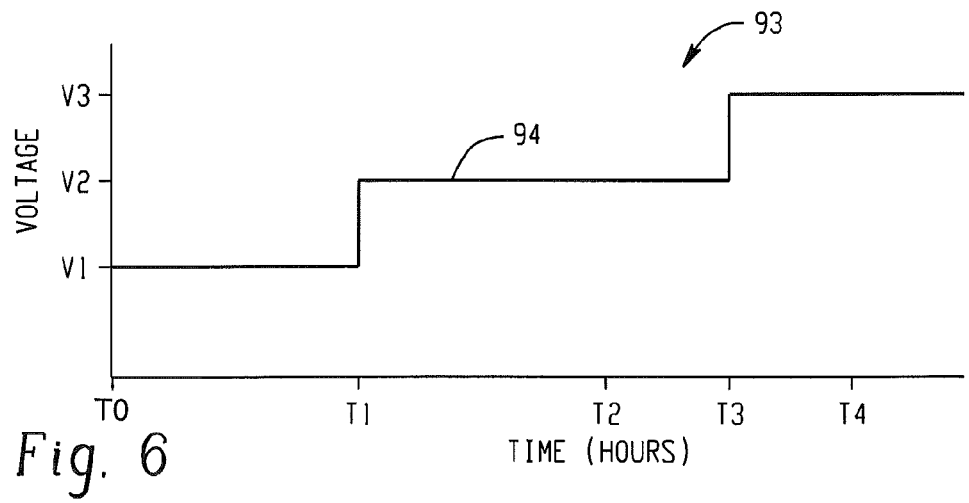
FIG. 6 is a graph having a curve illustrating exemplary voltages applied to a fan over time in the air freshener device of FIG. 1 to obtain the exemplary fan speeds illustrated in FIG. 5.
Figure 7:
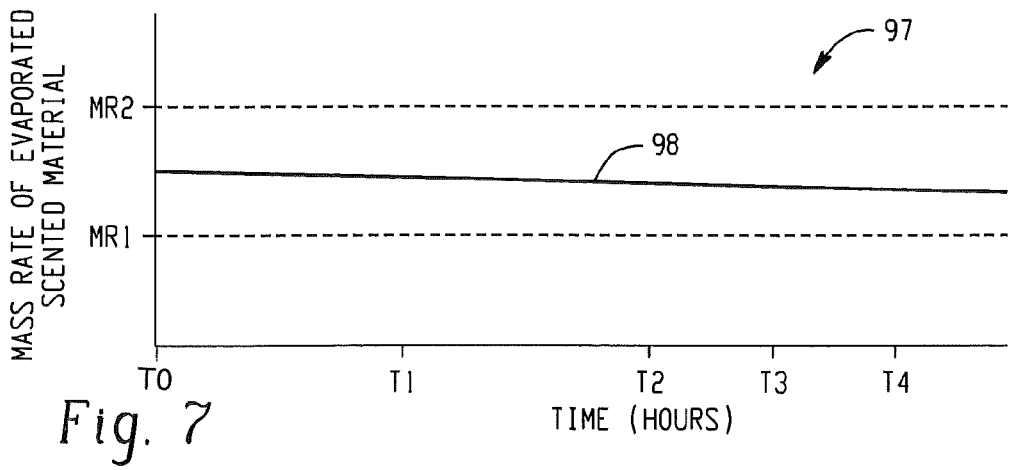
FIG. 7 is a graph having a curve illustrating exemplary mass rates of evaporated scented material emitted from the air freshener of FIG. 1 in response to the exemplary fan speeds illustrated in FIG. 5.

Referring to FIGS. 5-7, with periodic reference to FIG. 1, exemplary graphs will be utilized to explain the first method for controlling an amount of evaporated scented material 34 emitted from the air freshener device 10. Graph 89 includes a curve 90 illustrating exemplary fan speeds of the fan 30 over time associated with the air freshener device 10. As shown, from time T0 to time T1, the fan speed is equal to rotational speed S1. Thereafter, from time T1 to time T2, the fan speed is increased to rotational speed S2, which is greater than rotational speed S1. Further, from time T2 to time T3, the fan speed is increased to rotational speed S3, which is greater than rotational speed S2.

Graph 93 includes a curve 94 illustrating exemplary voltages applied to the motor 28 over time in the air freshener device 10 to obtain the exemplary fan speeds illustrated in graph 89. As shown, from time T0 to time T1, the voltage is equal to voltage level V1. Thereafter, from time T1 to time T2, the voltage is increased to voltage level V2, which is greater than voltage level V1. Further, from time T2 to time T3, the voltage is increased to voltage level V3, which is greater than voltage level V2.

Graph 97 includes a curve 98 illustrating exemplary mass rates of evaporated scented material 34 emitted from the air freshener device 10 in response to the exemplary fan speeds illustrated in graph 89. As shown, from time T1 to time T4, the mass rate of evaporated scented material 34 is maintained within a desired mass rate range of mass rate MR1 to mass rate MR2.

Figure 8:
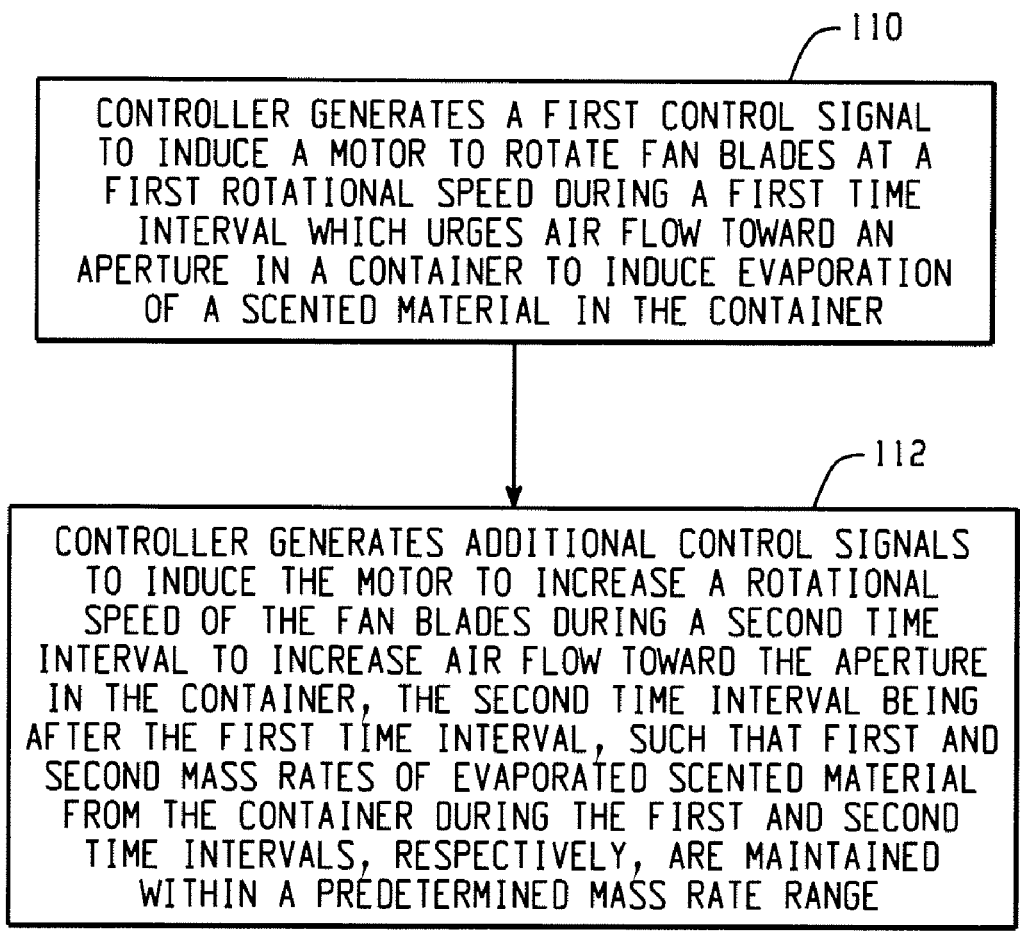
FIG. 8 is a flowchart of a method for controlling an amount of evaporated scented material emitted from the air freshener device of FIG. 1 in accordance with another exemplary embodiment.

Referring to FIG. 8, with periodic reference to FIGS. 1 and 2, a flowchart of the first method for controlling an amount of evaporated scented material 34 from the air freshener device 10 in accordance with another exemplary embodiment will now be explained.

At step 110, the controller 24 generates a first control signal to induce the motor 28 to rotate fan blades 68, 70 at a first rotational speed during a first time interval which urges air flow toward the aperture 80 in the container 32 to induce evaporation of the scented material 34 in the container 32.

At step 112, the controller 24 generates additional control signals to induce the motor 28 to increase a rotational speed of the fan blades 68, 70 during a second time interval to increase air flow toward the aperture 80 in the container 32, the second time interval being after the first time interval, such that first and second mass rates of evaporated scented material 34 from the container 32 during the first and second time intervals, respectively, are maintained within a predetermined mass rate range.

Before providing a detailed explanation of a second method for controlling an amount of evaporated scented material 34 emitted from the air freshener device 10, a brief overview of the methodology will be explained. The inventor herein has recognized that by increasing a percentage of time that the fan 30 is activated over an operational life of the air freshener device 10, a mass rate of evaporated scented material 34 from the air freshener device 10 can be maintained within a predetermined or desired mass rate range. In other words, the inventor herein has recognized that by increasing a percentage of time that the fan 30 is activated over the operational life of the air freshener device 10, the scent load or detectable scent emitted from the air freshener device 10 can be maintained within a desired scent load range.

Figure 9:
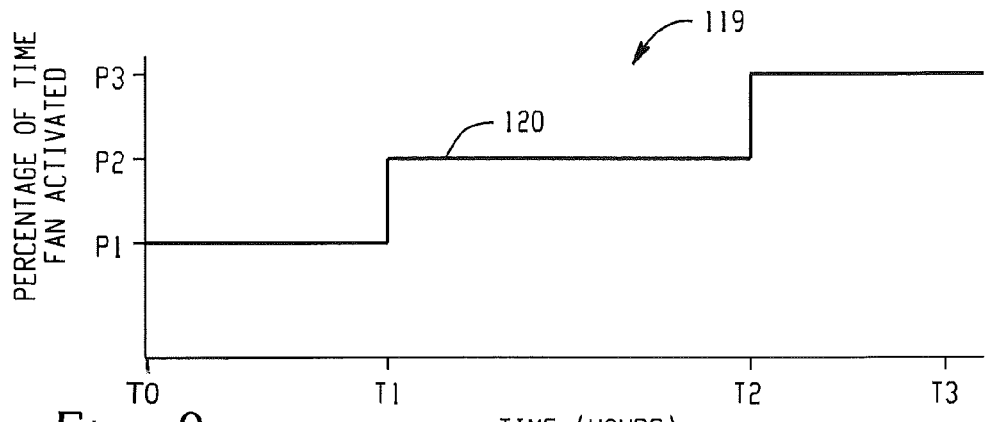
FIG. 9 is a graph having a curve illustrating exemplary percentages of time a fan is activated in the air freshener device of FIG. 1.
Figure 10:
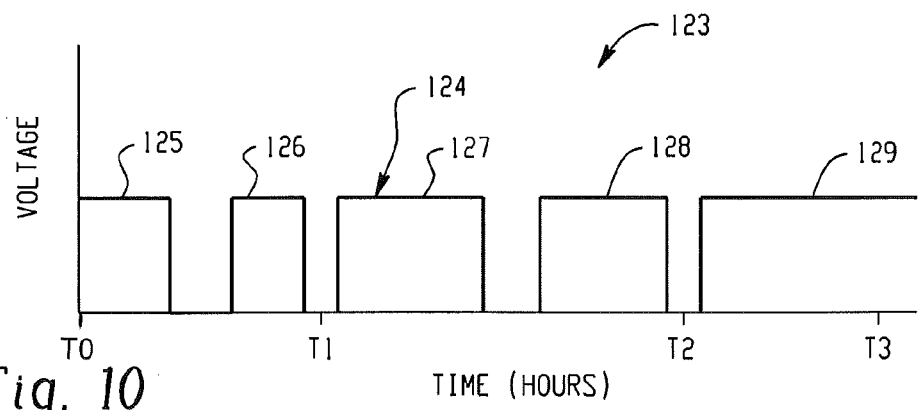
FIG. 10 is a graph having a curve illustrating exemplary voltages applied to a fan over time in the air freshener device of FIG. 1.
Figure 11:
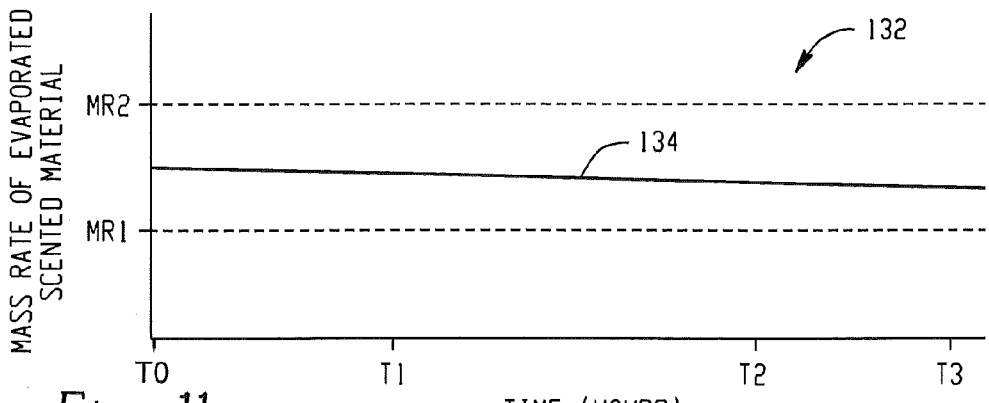
FIG. 11 is a graph having a curve illustrating exemplary mass rates of evaporated scented material emitted from the air freshener of FIG. 1 in response to the exemplary percentages of time the fan is activated illustrated in FIG. 9.

Referring to FIGS. 9-11, with periodic reference to FIGS. 1 and 2, exemplary graphs will be explained that will be useful in understanding the second method for controlling an amount of evaporated scented material 34 emitted from the air freshener device 10. Graph 119 includes a curve 120 illustrating exemplary percentages of time the fan 30 is activated in the air freshener device 10. As shown, from time T0 to time T1, the percentage of time that the fan 30 is activated is equal to the percentage P1. Thereafter, from time T1 to time T2, the percentage of time that the fan 30 is activated is increased to the percentage P2, which is greater than the percentage P1. Further, from time T2 to time T3, the percentage of time that the fan 30 is activated is increased to the percentage P3, which is greater than the percentage P2.

Graph 123 includes a curve 124 illustrating exemplary voltages applied to the motor 28 over time in the air freshener device 10 to obtain the exemplary percentages of time of fan activation illustrated in graph 119. As shown, from time T0 to time T1, voltage pulses 125, 126 are applied. Thereafter, from time T1 to time T2, voltage pulses 127, 128 are applied to the motor 28. Further, from time T2 to time T3, voltage pulse 129 is applied to the motor 28.

Graph 132 includes a curve 134 illustrating exemplary mass rates of evaporated scented material 34 emitted from the air freshener device 10 in response to the exemplary percentages of time that the fan 30 is activated as illustrated in graph 119. As shown, from time T1 to time T4, the mass rate of evaporated scented material 34 is maintained within a desired mass rate range of mass rate MR1 to mass rate MR2.

Figure 2:
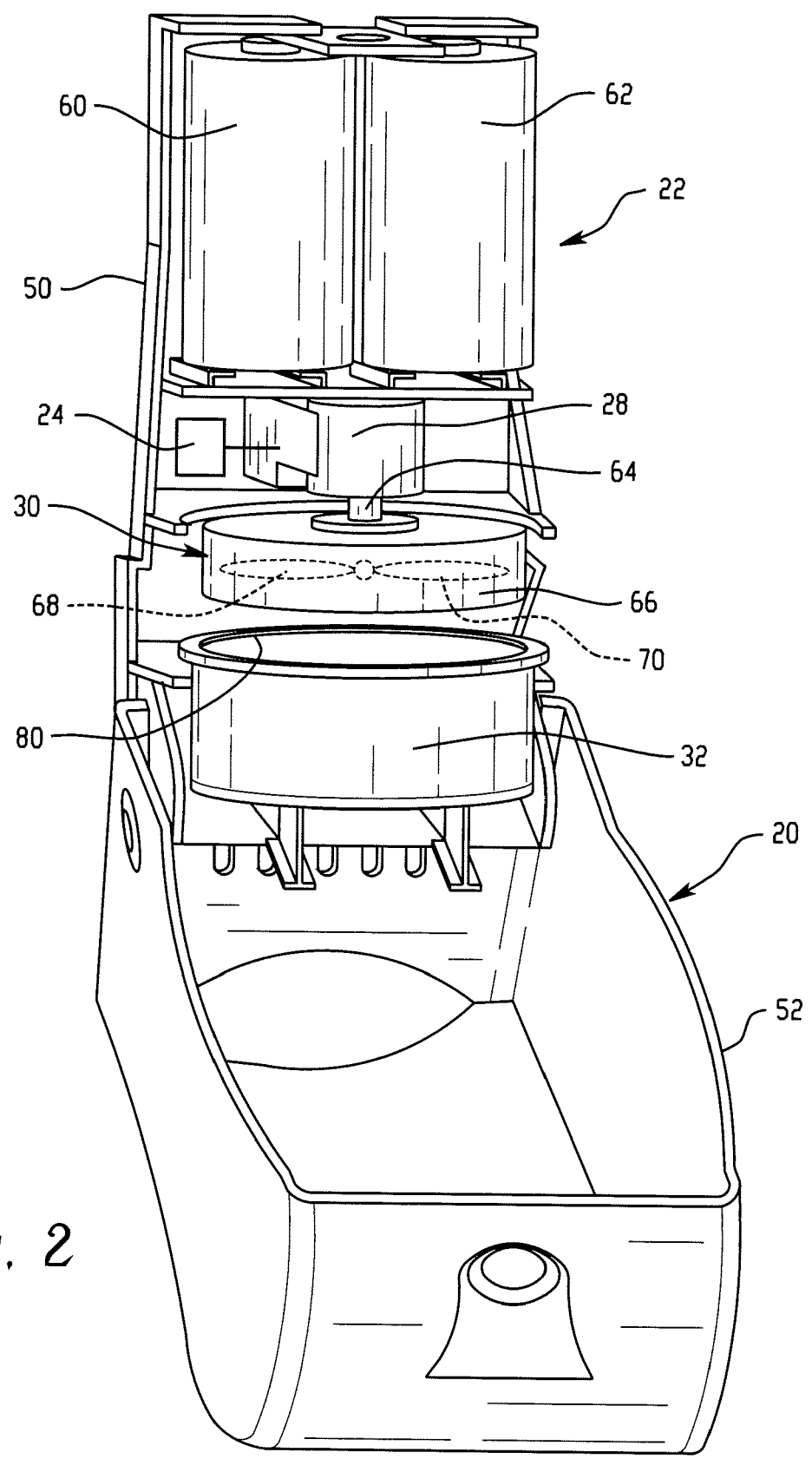
FIG. 2 is a detailed schematic of an interior of the air freshener device of FIG. 1.
Figure 3:
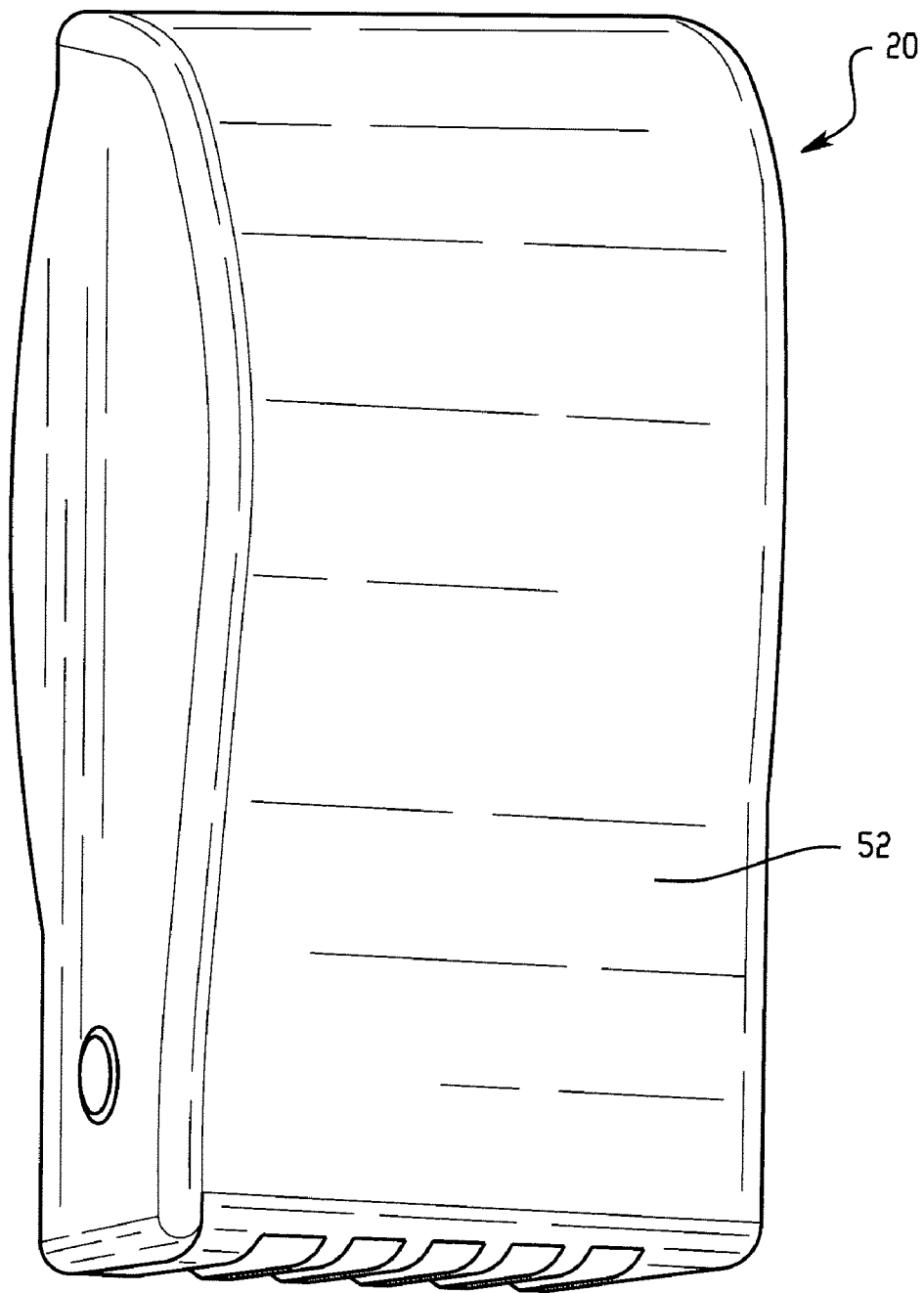
FIG. 3 is a schematic of a housing of the air freshener device of FIG. 2.
Figure 4:
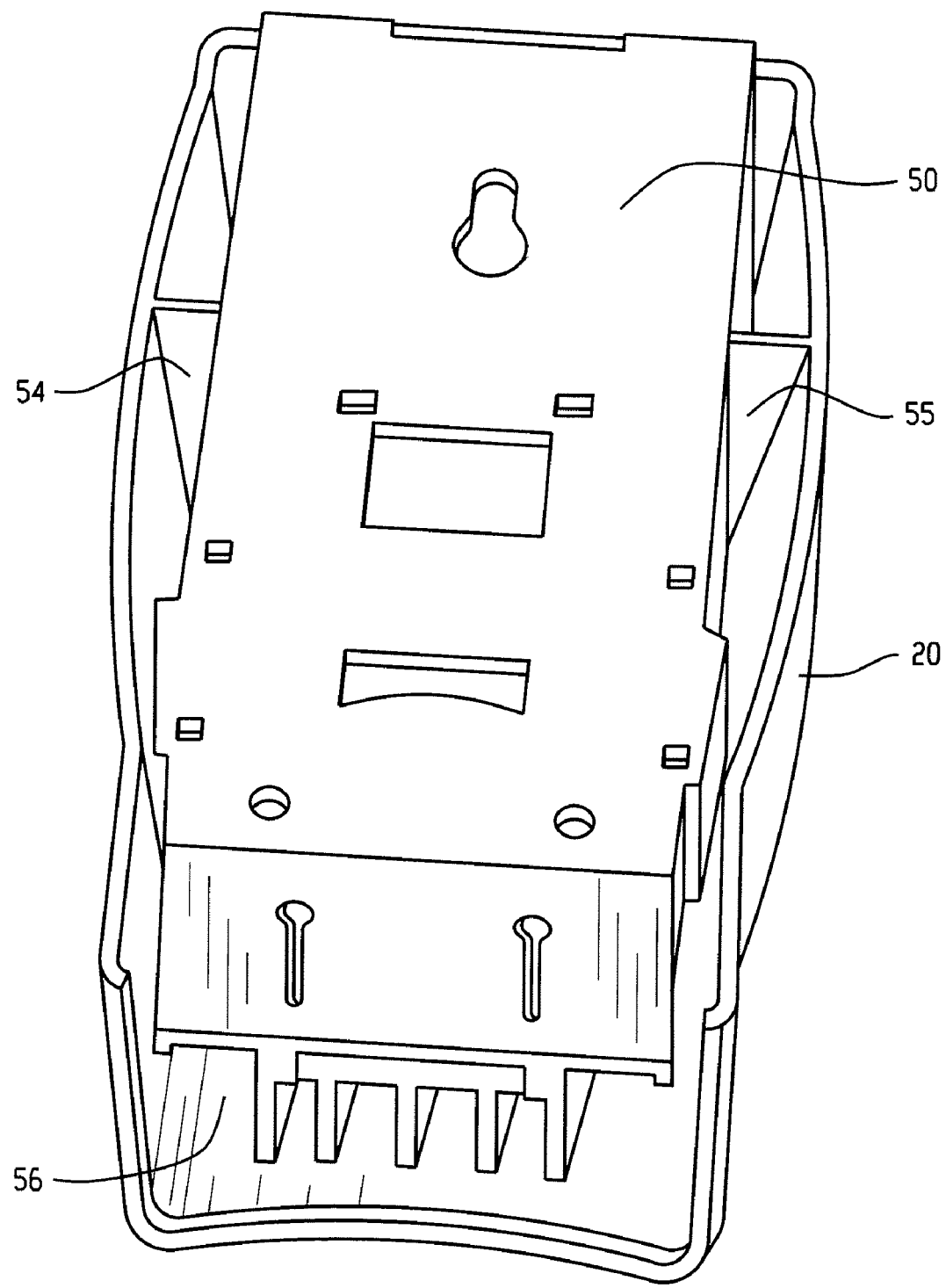
FIG. 4 is a schematic of a back plate and a portion of a housing of the air freshener device of FIG. 2.
Figure 12:
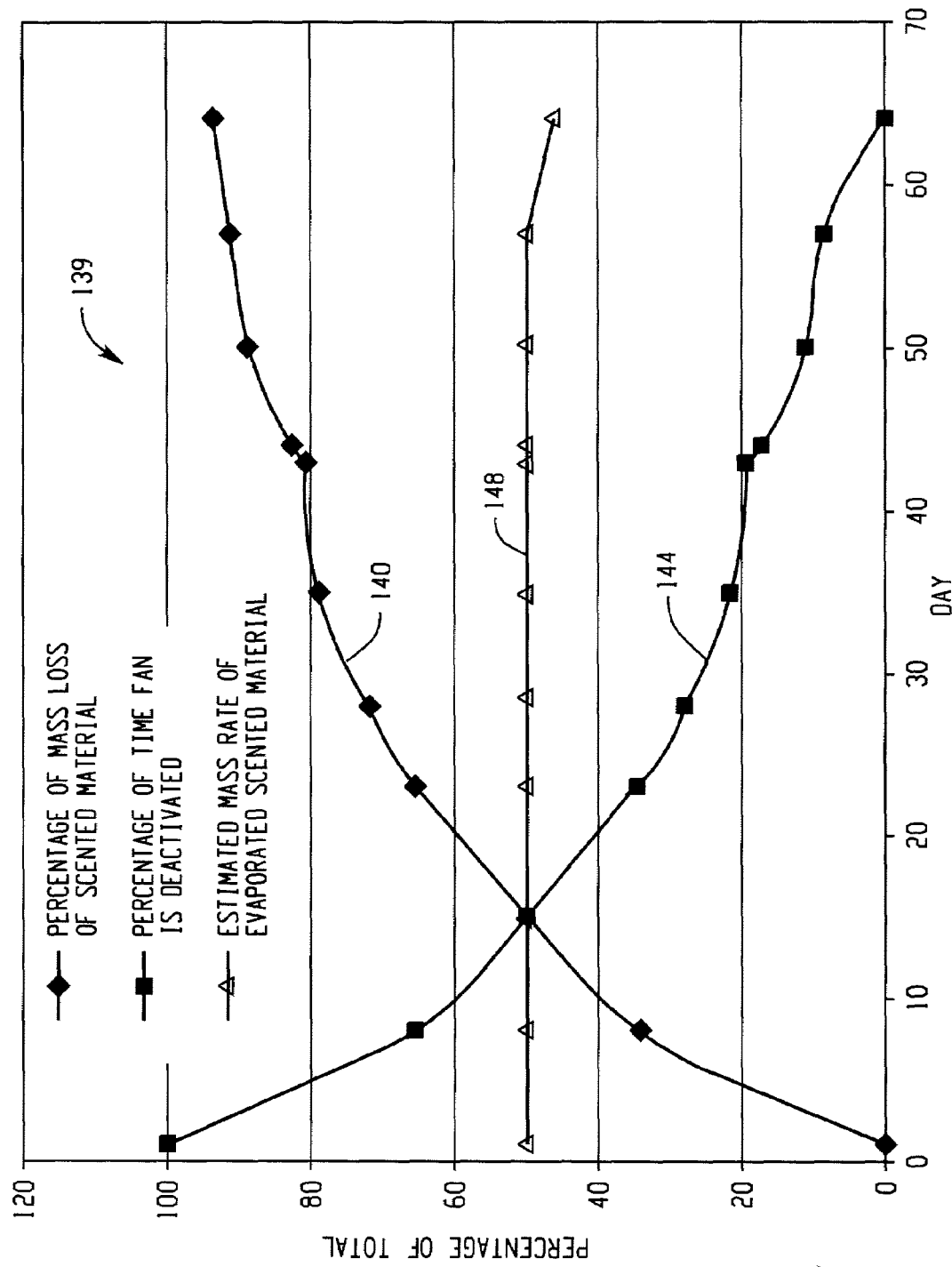
FIG. 12 is a graph having a first curve illustrating a percentage of mass loss of scented material over an operational life of the air freshener device of FIG. 1, a second curve illustrating a percentage of time a fan is deactivated over the operational life of the air freshener device of FIG. 1, and a third curve indicating an estimated mass rate of evaporated scented material over the operational life of the air freshener device of FIG. 1.

Referring to FIG. 12, with periodic reference to FIGS. 1 and 2, an exemplary graph 139 that is useful in understanding the second method for controlling an amount of evaporated scented material 34 emitted from the air freshener device 10 is illustrated. The graph 139 includes a curve 140 illustrating a percentage of mass loss of the scented material 34 over an operational life of the air freshener device 10. The graph 139 further includes an exemplary curve 144 illustrating a percentage of time the fan 30 is deactivated over the operational life of the air freshener device 10. As shown, as the air freshener device 10 ages, the percentage of time that the fan 30 is deactivated is decreased. The graph 139 further includes an exemplary curve 148 that illustrates an estimated mass rate of evaporated scented material 34 from the air freshener device 10 over the operational life of the air freshener device 10.

Figure 13:
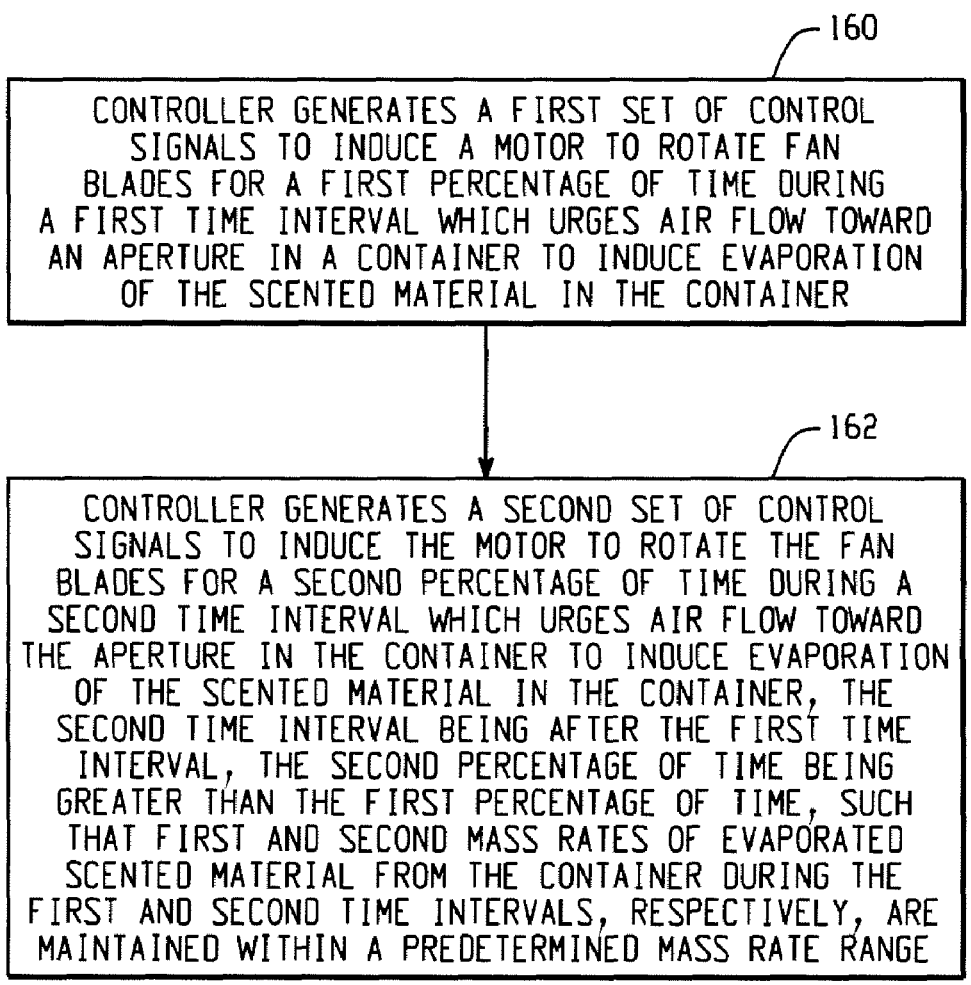
FIG. 13 is a flowchart of a method for controlling an amount of evaporated scented material emitted from the air freshener device of FIG. 1 in accordance with another exemplary embodiment.

Referring to FIG. 13, with periodic reference to FIGS. 1 and 2, a flowchart of the second method for controlling an amount of evaporated scented material 34 from the air freshener device 10 in accordance with another exemplary embodiment will now be explained.

At step 160, the controller 24 generates a first set of control signals to induce the motor 28 to rotate fan blades 68, 70 for a first percentage of time during a first time interval which urges air flow toward the aperture 80 in the container 32 to induce evaporation of the scented material 34 in the container 32.

At step 162, the controller 24 generates a second set of control signals to induce the motor 28 to rotate the fan blades 68, 70 for a second percentage of time during a second time interval which urges air flow toward the aperture 80 in the container 32 to induce evaporation of the scented material 34 in the container 32, the second time interval being after the first time interval, the second percentage of time being greater than the first percentage of time, such that first and second mass rates of evaporated scented material 34 from the container 32 during the first and second time intervals, respectively, are maintained within a predetermined mass rate range.

The air freshener device and methods for controlling an amount of evaporated scented material from the air freshener device represent a substantial advantage over other devices and methods. In particular, the air freshener device and methods provide a technical effect of maintaining a predetermined mass rate range of evaporated scented material over an operational life of the air freshener device.

While the invention has been described with reference to exemplary embodiments, it will be understood by those skilled in the art that various changes may be made and equivalent elements may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiments disclosed for carrying this invention, but that the invention will include all embodiments falling within the scope of the appended claims. Moreover, the use of the terms, first, second, etc. are used to distinguish one element from another. Furthermore, the use of the terms a, an, etc. do not denote a limitation of quantity, but rather denote the presence of at least one of the referenced items.

What is claimed is:

1. A method for controlling an amount of evaporated scented material emitted from an air freshener device, the air freshener device having a container, a motor, and fan blades coupled to the motor, the container having an aperture and holding a scented material therein, the method comprising:

generating a first control signal to induce the motor to rotate the fan blades at a first rotational speed during a first time interval which urges air flow toward the aperture of the container to induce evaporation of the scented material in the container; and generating additional control signals to induce the motor to increase a rotational speed of the fan blades during a second time interval to increase air flow toward the aperture of the container, the second time interval being after the first time interval, such that first and second mass rates of evaporated scented material from the container during the first and second time intervals, respectively, are maintained within a predetermined mass rate range.

2. The method of claim 1, wherein the scented material is at least one of a scented gel, a scented liquid, a scented solid material, and a scented semi-solid material.

3. The method of claim 1, wherein the generating additional control signals to induce the motor to increase the rotational speed of the fan blades comprises generating additional control signals to induce the motor to non-linearly increase the rotational speed of the fan blades.

4. The method of claim 1, wherein:
the generating a first control signal comprises generating a first control signal to induce the motor to rotate the fan blades at a first constant rotational speed during a first time interval; and
the generating additional control signals comprises generating a second control signal to induce the motor to rotate the fan blades at a second constant rotational speed during a second time interval, the second constant rotational speed being greater than the first constant rotational speed, and the second time interval being contiguous with and subsequent to the first time interval.

5. The method of claim 4, wherein:
the generating additional control signals comprises generating a third control signal to induce the motor to rotate the fan blades at a third constant rotational speed during a third time interval, the third constant rotational speed being greater than the second constant rotational speed, and the third time interval being contiguous with and subsequent to the second time interval.

6. The method of claim 5, wherein:
the first control signal results in a first constant voltage being applied to the motor; and
the second control signal results in a second constant voltage being applied to the motor, the second constant voltage being greater than the first constant voltage.

7. The method of claim 6, wherein:
the third control signal results in a third constant voltage being applied to the motor, the third constant voltage being greater than the second constant voltage.

8. An air freshener device, comprising:
a container holding scented material therein, the container having an aperture;
a motor coupled to fan blades, the motor configured to rotate the fan blades; and
a controller operably coupled to the motor, the controller configured to generate a first control signal to induce the motor to rotate the fan blades at a first rotational speed during a first time interval which urges air flow toward the aperture of the container to induce evaporation of the scented material in the container, the controller further configured to generate additional control signals to induce the motor to increase a rotational speed of the fan blades during a second time interval to increase air flow toward the aperture of the container, the second time interval being after the first time interval, such that first and second mass rates of evaporated scented material from the container during the first and second time intervals, respectively, are maintained within a predetermined mass rate range.

9. The air freshener device of claim 8, wherein the scented material is at least one of a scented gel, a scented liquid, a scented solid material, and a scented semi-solid material.

10. The air freshener device of claim 8, wherein the controller configured to generate additional control signals to induce the motor to increase the rotational speed of the fan blades comprises the controller configured to generate the additional control signals to non-linearly increase the rotational speed of the fan blades.

11. The air freshener of claim 8, wherein:
the first control signal comprises a first control signal to induce the motor to rotate the fan blades at a first constant rotational speed during a first time interval; and
the control signals comprises a second control signal to induce the motor to rotate the fan blades at a second constant rotational speed during a second time interval, the second constant rotational speed being greater than the first constant rotational speed, and the second time interval being contiguous with and subsequent to the first time interval.

12. The air freshener of claim 11, wherein:
the additional control signals comprises a third control signal to induce the motor to rotate the fan blades at a third constant rotational speed during a third time interval, the third constant rotational speed being greater than the second constant rotational speed, and the third time interval being contiguous with and subsequent to the second time interval.

13. The air freshener of claim 12, wherein:
the first control signal results in a first constant voltage being applied to the motor; and
the second control signal results in a second constant voltage being applied to the motor, the second constant voltage being greater than the first constant voltage.

14. The air freshener of claim 13, wherein:
the third control signal results in a third constant voltage being applied to the motor, the third constant voltage being greater than the second constant voltage.

* * * * *